(12) United States Patent
Herzog

(10) Patent No.: US 8,419,424 B2
(45) Date of Patent: Apr. 16, 2013

(54) FUNCTIONAL ORTHODONTIC APPLIANCE WITH AN EXTRAORAL DEVICE

(76) Inventor: Guido Herzog, Winterthur (CH)

(*) Notice: Subject to any disclaimer, the term of this patent is extended or adjusted under 35 U.S.C. 154(b) by 2273 days.

(21) Appl. No.: 10/508,189

(22) PCT Filed: Mar. 6, 2003

(86) PCT No.: PCT/CH03/00155
§ 371 (c)(1), (2), (4) Date: Sep. 17, 2004

(87) PCT Pub. No.: WO03/077787
PCT Pub. Date: Sep. 25, 2003

(65) Prior Publication Data
US 2007/0117062 A1 May 24, 2007

(30) Foreign Application Priority Data
Mar. 18, 2002 (CH) .......................... 468/02

(51) Int. Cl.
A61C 7/06 (2006.01)

(52) U.S. Cl.
USPC .................................. 433/5; 433/6

(58) Field of Classification Search .......... 433/5, 6, 433/18–22
See application file for complete search history.

(56) References Cited

U.S. PATENT DOCUMENTS

| 2,880,509 | A | | 4/1959 | Strickler | |
|---|---|---|---|---|---|
| 3,814,087 | A | * | 6/1974 | Heikes | 602/36 |
| 4,038,754 | A | * | 8/1977 | Armstrong | 433/5 |
| 4,431,411 | A | * | 2/1984 | Witzig et al. | 433/6 |
| 4,439,148 | A | * | 3/1984 | Haas | 433/5 |
| 4,637,796 | A | * | 1/1987 | Korn | 433/7 |
| 4,815,972 | A | * | 3/1989 | Howe | 433/5 |
| 4,881,896 | A | * | 11/1989 | Bergersen | 433/5 |
| 5,159,359 | A | * | 10/1992 | Pauly et al. | 351/128 |

FOREIGN PATENT DOCUMENTS

| DE | 12 81 105 B | 10/1968 |
|---|---|---|
| DE | 34 11 297 A | 10/1985 |
| EP | 0 364 652 A | 4/1990 |

* cited by examiner

Primary Examiner — Cris L Rodriguez
Assistant Examiner — Edward Moran
(74) Attorney, Agent, or Firm — Ziolkowski Patent Solutions Group, SC

(57) ABSTRACT

A functional orthodontic appliance including a facebow as an extraoral device for treating malpositions of the jaws or teeth. The functional orthodontic appliance includes a pad holder which is fastened to a transition area of the facebow and can be individually positioned and adjusted by very simple means. Preferably, the pad holder is provided with one pair of pads or a twin plate which is/are placed inside the lower lip in the vestibule that is displaced downward. The inventive appliance makes it possible to do functional orthodontic therapy of the lower jaw with all known advantages while correcting the position of the teeth in the upper jaw.

17 Claims, 5 Drawing Sheets

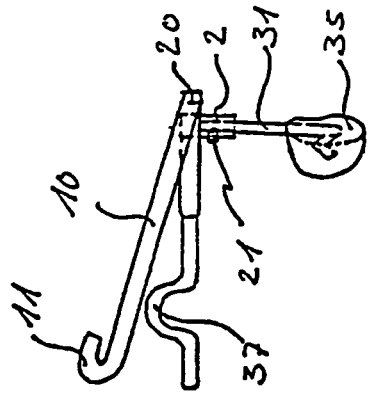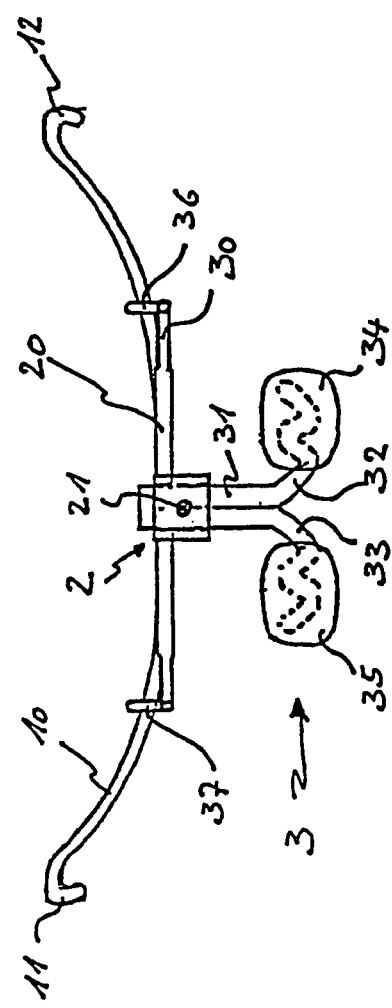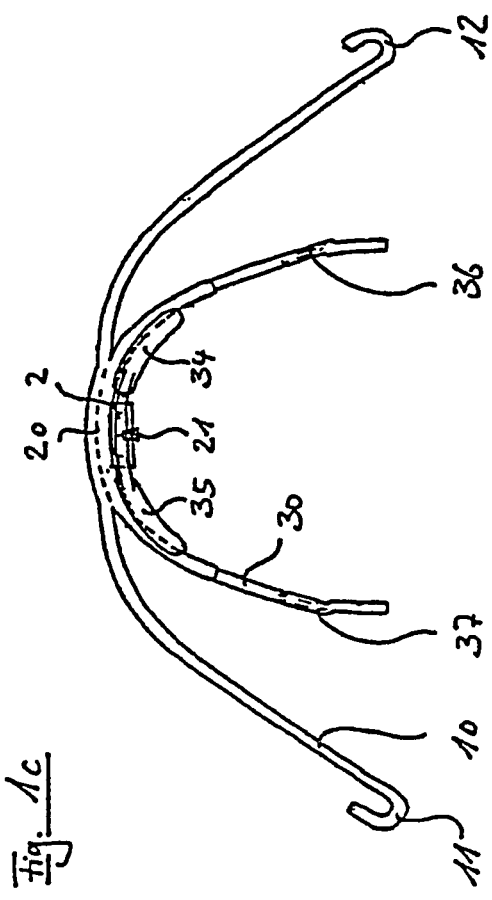

Fig. 4
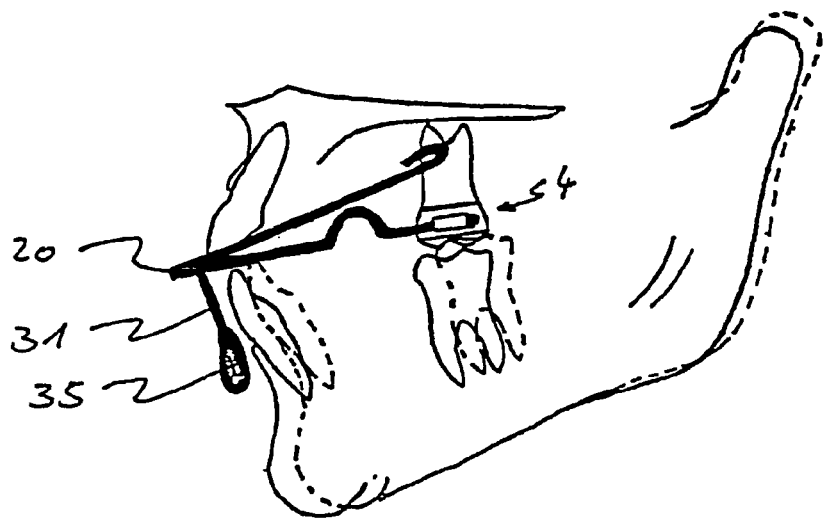
Fig. 5a
Fig. 5b
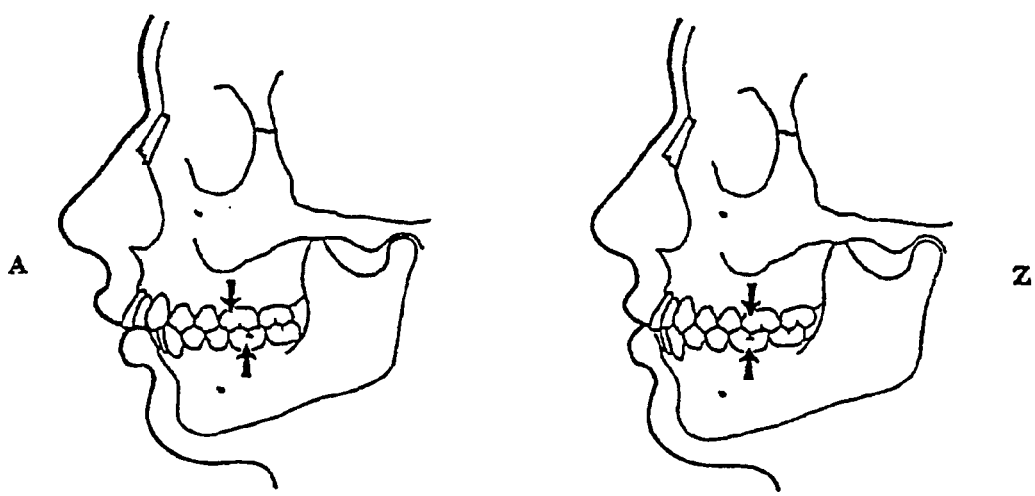

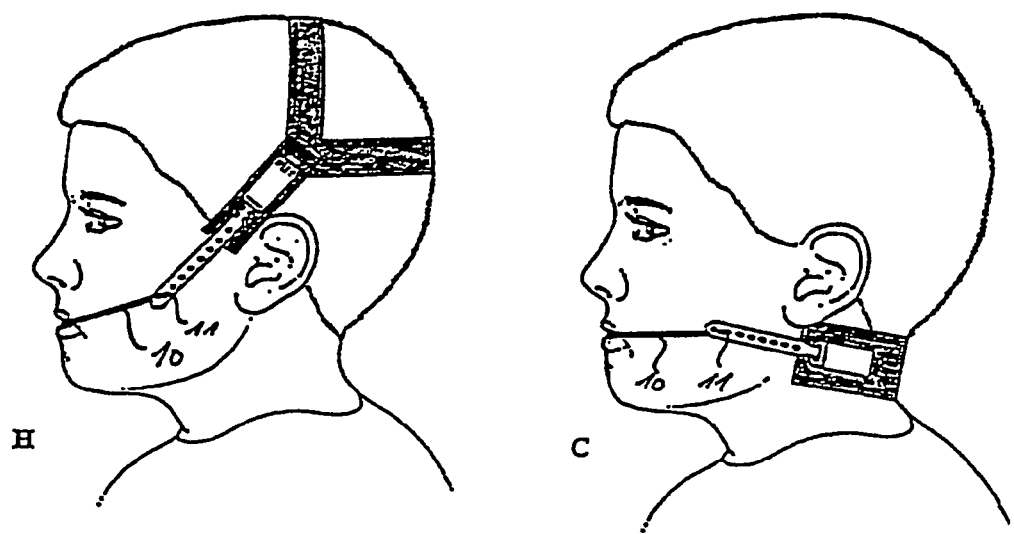

FUNCTIONAL ORTHODONTIC APPLIANCE WITH AN EXTRAORAL DEVICE

CROSS REFERENCE TO RELATED APPLICATION

The present application claims priority of International Application No. PCT/CH03/00155, which claims priority of Swiss Patent Application No. 468/02, filed Mar. 18, 2002.

BACKGROUND OF THE INVENTION

The present invention relates to a functional orthodontic appliance with an exraoral aid for treating malpositions of the jaw or teeth. Distal occlusion is a malposition of the jaw or teeth which often occurs. One cause is maxillary prognathisim which manifests itself in the protrusion of the upper jaw beyond its normal extent. The upper jaw is too large or is dislocated to the front in contrast to the normal occlusion or eugrathic occlusion. A second cause is a mandibular retrognathisim. This manifests itself by a retruded lower jaw. A third cause is maxillary dentoalveolar protrusion. It manifests itself in a protrusion of the teeth of the upper jaw when the jaw relation is correct. The treatment today is effected in a standard manner by way of orthodontic apparatus which are stationarily positioned or may be removed, or by way of functional orthodontic appliances (FO-appliances). An additional surgical orthodontic treatment is only required in particularly cases which are resistant to therapy.

The most varied of dentition regulators are known on the market under the collective term of FO-appliances, which although being based on similar active principles, however greatly vary in their manner of design and their constructional shape. Common to all FO-appliances is the fact that they act simultaneously on the upper and lower jaw and the correction of the malposition is achieved by way of a targeted diversion (deflection) of the muscular forces acting in the region of the mouth. The basis or therapy by way of FO-appliances lies in training away the restricting malfunctions of the muscle system, and thus a correction of the functional malposition of the lower jaw is achieved. Painful or damaging overloading of the tissue is avoided since the person being treated to a certain extent may meter the correcting force himself.

Known FO-for example include the activator according to Adresen and Häupl, the bionator according to Balters, the dentition shaper according to Bimler, the elastically-open activator according to Klammt, the kinetor according to Stockfisch, the cybernator, the denudated activator, the functionator (FIO), the twin-bloc appliance, the Zürcher activator to Teuscher, and the regulator according to Fränkel.

The apparatus which are often grouped under the term "activators" are more or less rigid appliances, which lie loosely in the mouth and have no fixed holding elements on the teeth. They must be held in a certain position by the muscle system and act as activators for the chewing and lip muscle system. Above all, the control of the growth of the jaw and the correction of the malposition of the upper and lower jaw to one another is to be achieved by way of this. For this, the muscular forces are diverted or directed in a desired direction so that the growth of the jaw is likewise effected in the desired position, finally resulting in the compensation of the malposition.

Since the success of the therapy depends on the growth, the FO-appliances are preferably applied with young and very young patients, to some extent still having milk teeth, but mainly having a mixed dentition, which entails very special problems with regard to their acceptance and discipline with regard to their wearing.

The function regulator according to Fränkel effects the correction of the jaw exclusively via the muscle system. Therapy with the Fränkel functional regulator necessitates a habitual phase in which the dysfunctional muscle system is trained and strengthened during the day by way of the Fränkel FO-appliance. This training is increased until in the actual treatment phase the appliance may be worn during the day and above all, also at night. The regression of the lower jaw is observed as a result of a functional and postural weakness of the muscle system. This is stimulated by way of a plate which on the inside below the front of the lower jaw bears on the lip, and is actively brought into the desired position by the wearer so that a sinking of the lower jaw is avoided. The plates do not serve as mechanical bearings, but they represent a mechanical stimulus which does not directly load the tissue. With the functional regulators according to Fränkel, apart from lip plates or pads, cheek plates having a large area are held distanced by a few millimeters from the jaw by way of a complex wire skeleton. Three to four of the Fränkel appliances are required for the complete treatment since adaptations of the individual apparatus to the growth of the jaw are not possible. With deciduous dentition, with the Fränkel appliance the problem of toothing inhibition occurs which may even lead to a stoppage of the therapy. The Fränkel function regulator may neither be combined with brackets nor with headgear.

If malpositions are present which may not be adequately treated with removable or fixed braces alone, then additional forces are introduced with extraoral appliances, preferably external braces or headgear. The main functions of the external brace lies in a) rearwardly correcting the position of lateral teeth in the upper jaw which project too much to the front, b) preventing correctly seated lateral teeth from sliding forward and c) retarding the upper jaw in growth with respect to the lower jaw. The external brace consists of a facebow and a head or neck strip. The facebow in turn is constructed of an inner and outer bow which in each case is formed of strong metal wires and are connected centrally in the transition region. The inner bow at its end region is detachably fastened on removable plates or stationary appliances. It is preferably inserted into small tubes which with strips are fastened to the molar teeth. The often thicker outer bow transmits the tensile forces from the strip system bearing on the head and/or neck (neck strip and/or head cap) onto the inner bow and thus onto the teeth in the lower jaw.

With regard to the head-car or Teuscher activator, the combination of a bimaxillary monoblock appliance with an outer bow is known as an extraoral aid for treating an extreme distocclusion. If such appliance, are used for a less acute prognathism, then at the location of the desired moderate correction however an overcompensation and an artificially induced protrusion of the lower jaw or other malpositions may occur.

The treatment with FO-appliances often lasts longer that of fixed appliances and for example only permits the targeted positional change of individual teeth to a limited extent. Known FO-appliances often entail great handicaps on speaking and their success is heavily dependent on the cooperation of the very often young patients. Furthermore they may not be used simultaneously with stationary (fixed) appliances.

BRIEF SUMMARY OF THE INVENTION

It is therefore the object of the present invention to provide an orthodontic appliance which has the advantages of known FO-appliances on treating a mandibular retrusion and simultaneously permits a targeted influencing of the teeth in the upperjaw.

This object is achieved by a functional orthodontic (FO) appliance having an extraoral facebow configured to treat malpositions of the jaw and teeth. The FO-appliance also includes a pad holder fastened on the facebow in a transition region, wherein the pad holder has at least one vertical arm which continues into at least one pad-carrying lateral arm positioned intraorally and that is vertically positioned relative to the extraoral facebow.

Further embodiment variants are to be deduced from the dependent claims

BRIEF DESCRIPTION OF THE DRAWINGS

One embodiment of the subject-matter of the invention is shown in the drawings and is explained in the subsequent description. There are shown in FIG. 1a a view from the inside (orally) or a growth-directing appliance according to a preferred embodiment of the present invention;

FIG. 1b a view from below (caudally) on the appliance according to FIG. 1a; and

FIG. 1c a lateral view (sagittally) of the apparatus according to FIGS. 1a and 1b.

FIG. 4 illustrates the difference of the lower jaw position relative to the upper jaw with and without growth guide appliance at the beginning of the treatment, wherein the lower jaw position is represented dashed without the applied device.

FIG. 5 shows an initial situation A with a lower lip interposition before the treatment and target position Z with a corrected sagittal overjet and relaxed lip position after completion of the treatment, and in FIG. 6 the appliance according to the invention supplemented by a high-pull head cap (H) or a cervical-pull neck strip (C) in an external view.

DETAILED DESCRIPTION OF THE INVENTION

Figure 2A:
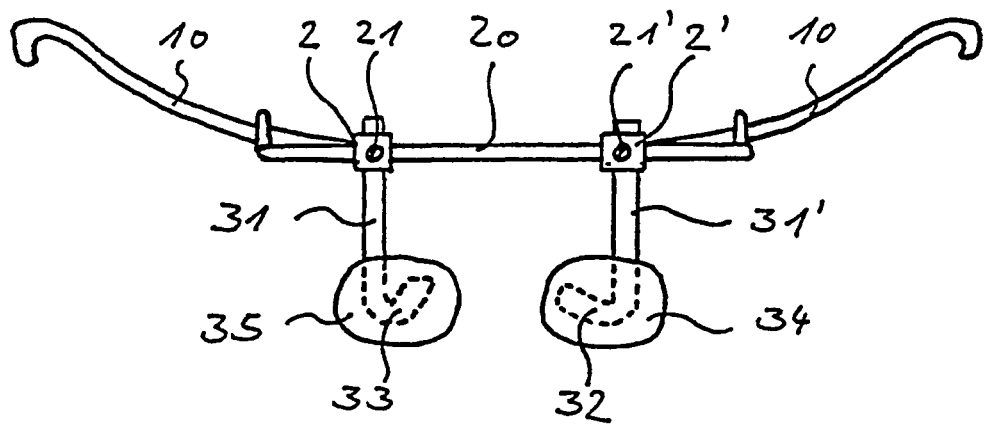
FIG. 2a to 2c show further preferred embodiments of pad holders according to the invention.

The central elements of a growth guide appliance (GGA) according to the present invention are shown in a preferred embodiment in FIG. 1. An essentially known facebow 1 with an outer bow 10 which runs on the outer side of the face approximately parallel to the cheeks is rigidly connected to an inner bow 30 in the transition region 20. The outer bow 10 at both ends comprises hooks 11, 12 which are detachably connectable directly or via known safety modules to the head and neck tension strips which are not shown in FIG. 1. The tensile forces acting on the outer bow 10, in the transition 20 are transmitted onto the inner bow 30 which is located in the oral cavity. The outer bow 10, the inner bow 30 and the transition 20 are designed such that the transition 20 is located in the cleft of the lip of the person to be treated so that the lips may be closed without restraint when the facebow 1 is applied. The inner bow 30 transmits the forces introduced from the outer bow directly onto the teeth or onto the known removable plate appliances which hereinafter are not described in more detail. On application of the facebow 1, the proximal ends 31, 32 of the inner bow 30 are pushed into tubelets envisaged for them, which are on the molar teeth or suitable receivers on plates. The resilience loops 36, 37 which may be seen in the lateral view serve for horizontally positioning the facebow 1. The facebow 1 is provided in the transition region 20 with a receiver 2 for the introduction and detachable fastening of a perioral pad holder 3. It is evident from FIG. 1 that the receiver 2 is arranged centrally on the inner side of the transition 20. It is preferably welded with the transition region and has an adequate vertical extension in order to prevent tilting or pivoting of the pad holder 3 which is held in it. In the shown embodiment example, the receiver 2 is essentially shaped as a rectangular sleeve which is provided with a central fixation screw for the detachable fastening of the Y-shaped pad holder 3.

A vertical limb 31 of the pad holder 3 is likewise designed rectangular in cross section corresponding to the rectangular shape of the receiver 2, so that the holder 3 may be pushed into the receiver with little or no play. The base of the vertical limb 31 may be fastened in a clamped manner with a fastening means 21, in the shown embodiment example with a threaded pin 21. The vertical limb 31 and the receiver 2 in each case are shaped in a flat rectangular manner. A twisting of the vertical arm in the receiver caused by torsional forces which may possibly occur is prevented in a simple manner by way of this shaping. The vertical limb 31 extends more or less perpendicularly downwards up to the forking and branches into two lateral limbs 32, 33 which each carry one pad 34, 35. The pads 34, 35 are manufactured of known plastic materials and the lateral limbs 32, 33 are preferably admitted or cast into the respective pad. In order to improve the seating of the pads on the flat wires 32, 33, the regions encompassed by the pad are preferably bent [at an angle] once or twice and by way of this have a wave shape.

The pad holder 3 according to FIG. 1 functionally represents a twin plate which lies orally of the lower lip in the vestibule displaced caudally and which according to the specific requirements may be adjusted vertically and in a limited manner sagittally relative to the headgear.

Further variants of the pad holders are shown in FIG. 2 which is described in the following.

Figure 3A:
FIG. 3 indicates a main indication for the use of the appliance according to the invention.
FIG. 3b shows the jaw region according to FIG. 2a with an applied appliance in an embodiment with a detachable fastening to the molar teeth and the cooperation with the lips.
Figure 3B:
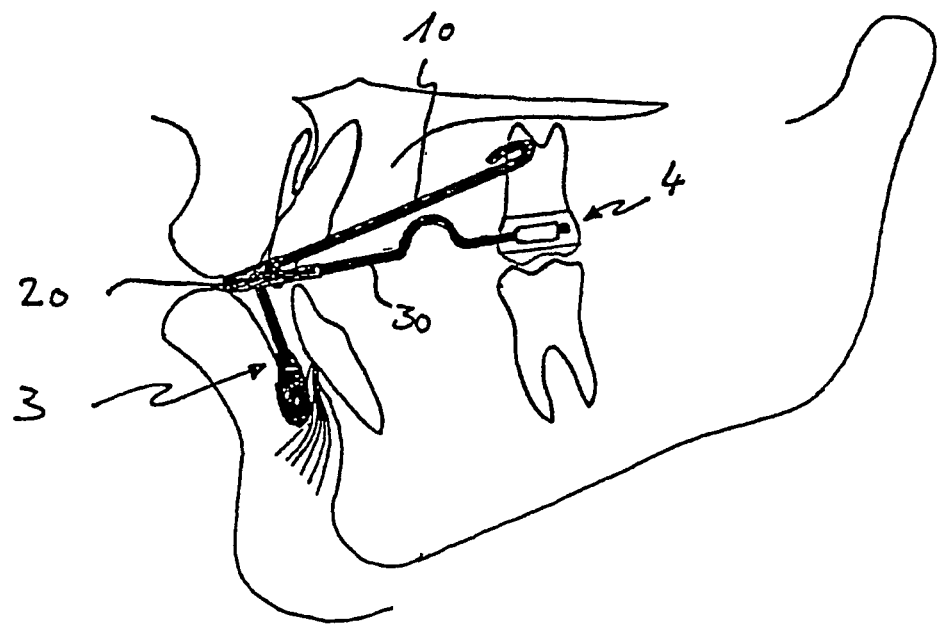

A main indication for the appliance according to the invention is shown in FIG. 3a. The interposition of the lower lip given an enlarged sagittal overjet with a moderate skeletal deviation is in need of but does not yet justify a significant operation such as the application of a bimaxillary monoblock apparatus. The manner of acting of the headgear and the pad holder 3 is illustrated in FIG. 3b. The lower jaw is guided in a classic FO manner into a desired ventral position by the two plastic pads or cushions 34, 35. The pads do not serve as counter bearings for the lower jaw but are rather to stimulate the patient into correcting the malposture himself. The pads 34, 35 lie deep in the vestibule. The upper and lower lip grip the headgear bow which together with the pad pair 3 correctly positions the lower lip and keeps it away from the front of the incisor. The disturbing forces of the lip and chewing muscle system are thus kept away from the lower jaw whilst upper lip may reinforce its influence. The pad holder 3 lies in the vestibule in front of the front or the lower jaw and actively displaces its arching. By way of individually setting its position in the sagittal and vertical dimension, the lower jaw may be guided into the desired position and by way of this one may achieve a positional change of the lower jaw in the rest position. The condyles are dislocated vertically-caudally. An increased growth of the lower jaw is stimulated by way of this and a change in the growth direction is rendered possible. The inner bow 30 in the shown embodiment variant is in tubelets which are fastened on strips 4 to the upper molars.

The appliance according to the present invention eliminates the restricting malfunction of the perioral muscle system and encourages the correction of the functional retral position of the lower jaw. By way of the loose and comfortable deflection of the lower jaw guided by the lower lip, the growth rate is encouraged and the redirection of the growth is diverted in a therapeutic manner. The toothing is led into the correct position by way of this.

A malfunction of the perioral muscle system is corrected by way of the position change and relaxation of the lower lip. The elimination of the muscular dysfunction permits a spontaneous regression and/or an elongation of the front teeth of the upper jaw, as well as a protrusion of the front teeth of the lower jaw. This permits the passive approximation of the front teeth and the part or complete accomplishment of the functionally correct front teeth relation. The aim is the creation of the equilibrium of the perioral muscle system. A long term stability of the front teeth relation is rendered possible by way of this.

This difference of the lower jaw position relative to the upper jaw at the beginning or the treatment (shown dashed) and after a treatment is illustrated in FIG. 4. The order of size of the lower jaw deflection is predefined by the sagittal position of the pad holder 3. With the above described main indication (initial situation A with lower lip interposition), as is shown in FIG. 5, the pad holder 3 may be positioned such that the desired target position Z with the correct sagittal overjet and relaxed lip position may be achieved in only one treatment step.

In contrast to the known FO-apparatus the pad holder according to the invention has the decisive advantage that the application may be carried out by the dentist or auxiliary personnel on location during the treatment. The costly and time-consuming manufacture of jaw models and wax registrates and the use of a dental laboratory is not required at all. The known individually designed and adapted appliances with plastic bodies and various wire parts are replaced by a premanufactured pad holder. The known facebows only need to be supplemented with a receiver means 2. The small increase in price which this entails is by all means accepted when taking into account the increased value which may be achieved.

The extremely inexpensive pad holders may be premanufactured in a few sizes and may be kept in supply by the every dentist with the minimal input of capital. A suitable pad holder is selected according to the age and size of the person to be treated and is fastened on the headgear 1. Additionally to the vertical adjustment possibility by way of the guide 2 and retaining means 21, the arms 31, 31', 32, 33, 33' may yet also be slightly bent and adjusted sagittally by way of this.

The pads 34, 35 are anatomically shaped, which is to say their size and shape is adapted to their application in the vestibulum oris. When required of course their relative position to one another may yet be adapted by way of bending the inner arms 32, 33, 33'. If it should become necessary to guide the lower jaw into the desired target position in more than one treatment step, then the vertical position and also the sagittal position of the pad holder 3 may be changed at any time.

In the outer view according to FIG. 6 it is indicated that in each case, depending on the jaw base angle and the inclination of the occlusion plane, the appliance according to the invention may be supplemented by a high-pull head cap (H) or a cervical-pull neck strip (C). The tensile force, as with conventional headgear is applied by way of safety release.

Figure 2B:
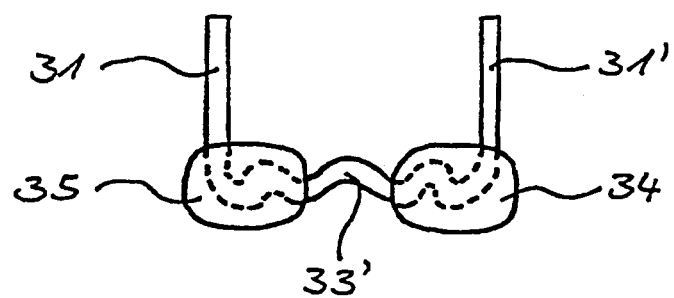
Figure 2C:
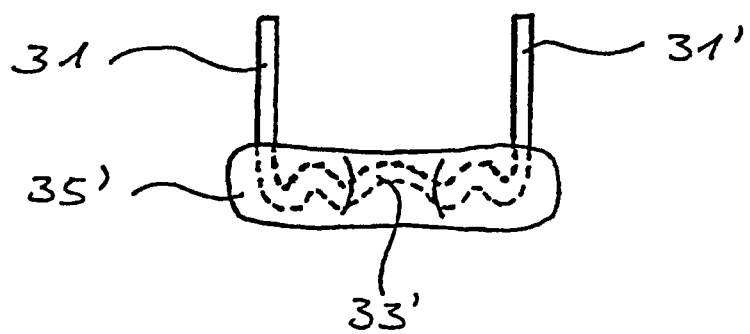

The headgear according to the invention differs from a conventional headgear thus to degree by the fastening possibility for a pad holder. Apart from the embodiment of the invention with a central guide 2 and a Y-shaped pad holder 3 represented in FIG. 1, advantageously, as shown in FIG. 2, one may also apply double-T shaped or U-shaped pad holders 3 which however each demand two receivers or guides 2 at the transition region 20 of the facebow 1. With the double I-shaped holder according to FIG. 2a, two separate vertical arms 31, 31' each carry a pad 35, 34. The pads by way of this may be positioned individually and independently of one another. With the U-shaped holder according to FIG. 2b, the vertical arms are connected via the lateral arm 33' and additionally stabilized. One embodiment form is shown in FIG. 2c, with which the U-shaped holder carries a continuous pad 35'.

In place of fixing the vertical position of the pad holder by way of an adjustment screw one may also use other forms of clamping, detachable or fixed connections between the vertical arm of the pad holder and the transition 20. The vertical arm may for example be fastened in a suitably shaped receiver sleeve 2 by way of crimping. A connection by way of welding, laser welding or gluing (bonding) is likewise possible.

The embodiment of FIG. 1 is however particularly preferred since it permits a positioning of the pad holder by way of the simplest of mechanical tools. The holder 3 is held vertically by way of a screwdriver, and when required may be bent in a fitting manner in the sagittal plane with a bending pliers or even by hand. As already mentioned above, the pad position may be adapted and changed at any time should problems with its wearing occur or with two-step treatments.

The shape and material selection of the appliance according to the invention permits a simple and thorough cleaning outside the mouth so that one may ensure perfect oral hygiene.

The invention claimed is:

1. An FO-appliance comprising:
   an extraoral facebow configured to treat malpositions of the jaw and teeth; and
   a pad holder fastened on the facebow in a transition region, wherein the pad holder has at least one vertical arm which continues into at least one pad-carrying lateral arm positioned intraorally and that is vertically positioned relative to the extraoral facebow;
   wherein the pad holder is Y-shaped, with a vertical arm which continues into two pad-carrying lateral arms that are configured to be inserted, vertically positioned, and fastened into a central receiver at the transition region.

2. The FO-appliance according to claim 1, wherein the vertical arm, at least in the fastening region, is shaped with a right-angled cross section, and that the central receiver is designed as a sleeve with a right-angled cross section.

3. The FO-appliance according to claim 1, wherein the vertical arm of the pad holder is fastened on the receiver at the transition region by way of a fastening manner being from the group of detachable clamp connections, crimping, soldering, welding, bonding, and gluing.

4. The FO-appliance according to claim 1, wherein the vertical arm is detachably fastenable in the receiver at the transition region by way of a threaded pin.

5. An FO-appliance comprising:
   an extraoral facebow configured to treat malpositions of the jaw and teeth; and
   a pad holder fastened on the facebow in a transition region, wherein the pad holder has at least one vertical arm which continues into at least one pad-carrying lateral arm positioned intraorally and that is vertically positioned relative to the extraoral facebow;
   wherein the transition region of the facebow comprises at least one receiver for fastening the pad holder; and wherein the pad holder is Y-shaped, with a vertical arm which continues into two pad-carrying lateral arms that are configured to be inserted, vertically positioned, and fastened into a central receiver at the transition region.

6. The FO-appliance according to claim 5, wherein the vertical arm, at least in the fastening region, is shaped with a right-angled cross section, and that the central receiver is designed as a sleeve with a right-angled cross section.

7. The FO-appliance according to claim 5, wherein the vertical arm of the pad holder is fastened on the receiver at the transition region by way of a fastening manner being from the group of detachable clamp connections, crimping, soldering, welding, bonding, and gluing.

8. The FO-appliance according to claim 5, wherein the vertical arm is detachably fastenable in the receiver at the transition region by way of a threaded pin.

9. The FO-appliance according to claim 5, wherein the at least one receiver is arranged on the inner side of the transition region.

10. An FO-appliance comprising:
    an extraoral facebow configured to treat malpositions of the jaw and teeth; and
    a pad holder fastened on the facebow in a transition region, wherein the pad holder has at least one vertical arm which continues into at least one pad-carrying lateral arm positioned intraorally and that is vertically positioned relative to the extraoral facebow;
    wherein the pad holder comprises at least one vertical arm that carries at least one pad; and
    wherein the pad holder is Y-shaped, with a vertical arm which continues into two pad-carrying lateral arms that are configured to be inserted, vertically positioned, and fastened into a central receiver at the transition region.

11. The FO-appliance according to claim 10, wherein the vertical arm, at least in the fastening region, is shaped with a right-angled cross section, and that the central receiver is designed as a sleeve with a right-angled cross section.

12. The FO-appliance according to claim 10, wherein the vertical arm of the pad holder is fastened on the receiver at the transition region by way of a fastening manner being from the group of detachable clamp connections, crimping, soldering, welding, bonding, and gluing.

13. The FO appliance according to claim 10, wherein the vertical arm is detachably fastenable in the receiver at the transition region by way of a threaded pin.

14. An FO-appliance comprising:
    an extraoral facebow configured to treat malpositions of the jaw and teeth; and
    a pad holder fastened on the facebow in a transition region, wherein the pad holder has at least one vertical arm which continues into at least one pad-carrying lateral arm positioned intraorally and that is vertically positioned relative to the extraoral facebow;
    wherein the pad holder is U-shaped or double I-shaped, with two vertical arms, that are inserted, vertically positioned, and fastened in two receivers on the transition region.

15. The FO-appliance according to claim 14, wherein the vertical arms of the pad holder are fastened on the receiver at the transition region by way of a fastening manner being from the group of detachable clamp connections, crimping, soldering, welding, bonding, and gluing.

16. The FO-appliance according to claim 14, wherein each vertical arm is detachably fastenable in a receiver at the transition region by way of a threaded pin.

17. The FO-appliance according to claim 14, wherein each vertical arm, at least in the fastening region, is shaped with a right-angled cross section, and that a corresponding receiver is designed as a sleeve with a right-angled cross section.

* * * * *

UNITED STATES PATENT AND TRADEMARK OFFICE
CERTIFICATE OF CORRECTION

PATENT NO. : 8,419,424 B2
APPLICATION NO. : 10/508189
DATED : April 16, 2013
INVENTOR(S) : Herzog It is certified that error appears in the above-identified patent and that said Letters Patent is hereby corrected as shown below:

In the Specifications

Col. 1, line 21, delete "eugrathic occlusion." and
substitute therefore -- eugnathic occlusion. --.

Col. 1, line 30, delete "cases which are resistant to therapy." and
substitute therefore -- difficult cases which are resistant to therapy. --.

Col. 1, line 39, delete "The basis or therapy" and
substitute therefore -- The basis of therapy --.

Col. 1, line 46, delete "Known FO-for" and
substitute therefore -- Known FO-appliances for --.

Col. 1, line 52, delete "to Teuscher, and the regulator" and
substitute therefore -- to Teuscher, and the functional regulator --.

Col. 2, line 16, delete "serve as mechanical bearings," and
substitute therefore -- serve as mechanical counter bearings, --.

Col. 2, line 48, delete "With regard to the head-car" and
substitute therefore -- With regard to the headgear --.

Col. 2, line 51, delete "If such appliance," and
substitute therefore -- If such appliances --.

Col. 3, line 20, delete "(orally) or" and
substitute therefore -- (orally) of --.

Signed and Sealed this
Sixteenth Day of July, 2013

Teresa Stanek Rea
*Acting Director of the United States Patent and Trademark Office*

CERTIFICATE OF CORRECTION (continued)
U.S. Pat. No. 8,419,424 B2

Col. 4, line 44, delete "deviation is in need of but" and
    substitute therefore -- deviation is in need of treatment but --.

Col. 4, line 56, delete "lower jaw whilst upper lip" and
    substitute therefore -- lower jaw whilst the upper lip --.

Col. 4, line 58, delete "of the front or" and
    substitute therefore -- of the front of --.

Col. 4, line 66, delete "variant is in tubelets" and
    substitute therefore -- variant is inserted in tubelets --.

Col. 5, line 22, delete "and after a treatment" and
    substitute therefore -- and after a successful treatment --.

Col. 5, line 64, delete "applied by way of safety release." and
    substitute therefore -- applied by way of a safety release. --.

Col. 5, line 66, delete "conventional headgear thus to degree" and
    substitute therefore -- conventional headgear thus to first degree --.